(12) United States Patent
Li et al.

(10) Patent No.: US 11,879,820 B2
(45) Date of Patent: Jan. 23, 2024

(54) DROPLET-BASED MICROFLUIDIC RHEOMETER SYSTEM

(71) Applicant: THE REGENTS OF THE UNIVERSITY OF MICHIGAN, Ann Arbor, MI (US)

(72) Inventors: Yunzi Li, Ann Arbor, MI (US); Kevin R. Ward, Glen Alen, VA (US); Mark A. Burns, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 503 days.

(21) Appl. No.: 17/035,047

(22) Filed: Sep. 28, 2020

(65) Prior Publication Data

US 2021/0010916 A1 Jan. 14, 2021

Related U.S. Application Data

(62) Division of application No. 15/773,703, filed as application No. PCT/US2016/060445 on Nov. 4, 2016, now Pat. No. 10,845,284.

(Continued)

(51) Int. Cl.
*G01N 11/04* (2006.01)
*G01N 33/49* (2006.01)
*G01N 11/00* (2006.01)

(52) U.S. Cl.
CPC ......... *G01N 11/04* (2013.01); *G01N 33/4905* (2013.01); *G01N 2011/008* (2013.01);

(Continued)

(58) Field of Classification Search
CPC .... G01N 11/00; G01N 11/04; G01N 33/4905; G01N 2011/0066; G01N 2203/0089
See application file for complete search history.

(56) References Cited

U.S. PATENT DOCUMENTS

| 4,449,395 A | 5/1984 | Kurtz et al. |
| 7,188,515 B2 | 3/2007 | Burns et al. |

(Continued)

FOREIGN PATENT DOCUMENTS

| CN | 1737531 A | 2/2006 |
| CN | 101065187 A | 10/2007 |

(Continued)

OTHER PUBLICATIONS

International Application No. PCT/US2016/060445, International Search Report and Written Opinion, dated Feb. 22, 2017.

(Continued)

*Primary Examiner* — Brian J. Sines
(74) *Attorney, Agent, or Firm* — MARSHALL, GERSTEIN & BORUN LLP

(57) ABSTRACT

A droplet-based microfluidic rheometer system and method of use for real-time viscosity monitoring of blood coagulation is disclosed. Droplets of blood samples are generated in a microfluidic rheometer, and the size of the droplets is highly correlated to the sample viscosity. The size of the droplets can be determined optically using an inverted light microscope and a camera or using electrodes. The microfluidic rheometer systems provides viscosity measurements in less than a second and consumes less than 1 µl blood or plasma over an hour period. The viscosity measurements may be displayed and transmitted to the Internet or cloud storage.

12 Claims, 5 Drawing Sheets

Related U.S. Application Data

(60) Provisional application No. 62/251,832, filed on Nov. 6, 2015.

(52) U.S. Cl.
CPC .............. *G01N 2011/0066* (2013.01); *G01N 2203/0089* (2013.01)

(56) References Cited

U.S. PATENT DOCUMENTS

| | | | |
|---|---|---|---|
| 7,482,939 | B2 | 1/2009 | Wenzig et al. |
| 7,654,468 | B2 | 2/2010 | Vafai et al. |
| 7,730,766 | B2 | 6/2010 | Ryser et al. |
| 7,889,329 | B2 | 2/2011 | Petrich et al. |
| 8,056,398 | B2 | 11/2011 | Jakli et al. |
| 8,454,906 | B2 | 6/2013 | Mathies et al. |
| 8,961,903 | B2 | 2/2015 | Sadaba Champetier De Ribes et al. |
| 2006/0179923 | A1 | 8/2006 | Burns et al. |
| 2007/0243627 | A1 | 10/2007 | Takayama et al. |
| 2008/0014589 | A1 | 1/2008 | Link et al. |
| 2008/0311006 | A1 | 12/2008 | Bek et al. |
| 2011/0201009 | A1 | 8/2011 | Quake et al. |
| 2013/0048565 | A1* | 2/2013 | Fiering ............ G01N 33/491 210/660 |
| 2014/0197101 | A1* | 7/2014 | Harjes ............ B81B 7/0009 210/321.66 |
| 2015/0044696 | A1 | 2/2015 | Dothie et al. |

FOREIGN PATENT DOCUMENTS

| | | |
|---|---|---|
| CN | 101183113 A | 5/2008 |
| CN | 201152848 Y | 11/2008 |
| CN | 101421608 A | 4/2009 |
| CN | 101819124 A | 9/2010 |
| CN | 102095670 A | 6/2011 |
| CN | 102147390 A | 8/2011 |
| CN | 201974361 U | 9/2011 |
| CN | 102266734 A | 12/2011 |
| CN | 102486446 A | 6/2012 |
| CN | 103143405 A | 6/2013 |
| CN | 103244598 A | 8/2013 |
| CN | 103833549 A | 6/2014 |
| CN | 203625276 U | 6/2014 |
| CN | 103988077 A | 8/2014 |
| CN | 103998928 A | 8/2014 |
| CN | 104198690 A | 12/2014 |
| EP | 1864107 A1 | 12/2007 |
| JP | S59124405 A | 7/1984 |
| WO | WO-2008/076399 A2 | 6/2008 |

OTHER PUBLICATIONS

International Preliminary Report on Patentability received in International Application No. PCT/US2016/060445, dated May 8, 2018.
Srivastava et al., Nanoliter viscometer for analyzing blood plasma and other liquid samples, Anal. Chem., 77(2):383-92 (Jan. 2005).
Srivastava et al., Electronic drop sensing in microfluidic devices: automated operation of a nanoliter viscometer, Lab Chip, 6(6):744-51 (Jun. 2006).
Livak-Dahl et al., Nanoliter droplet viscometer with additive-free operation, Lab Chip, 13:297-301 (2013).
DeLaMarre et al., Development of a Simple Droplet-Based Microfluidic Capillary Viscometer for Low-Viscosity Newtonian Fluids, Anal. Chem., 87: 4649-4657 (2015).
Chinese Patent Application No. 201680064505.1, Office Action, dated Jan. 11, 2021.
Laun et al., Guidelines for checking performance and verifying accuracy of rotational rheometers: viscosity measurements in steady and oscillatory shear (IUPAC Technical Report), Pure and Applied Chemistry, 86(12):1945-68 (2014).

* cited by examiner

DROPLET-BASED MICROFLUIDIC RHEOMETER SYSTEM

CROSS-REFERENCE TO RELATED APPLICATIONS

This application is a divisional application of U.S. application Ser. No. 15/773,703, filed May 4, 2018, which is a national phase of PCT/US16/60445, filed Nov. 4, 2016, which claims the benefit of the filing date of U.S. Provisional Application No. 62/251,832, filed Nov. 6, 2015, which are hereby incorporated by reference in their entireties.

FIELD OF THE DISCLOSURE

This application relates to a droplet-based microfluidic rheometer system for real-time viscosity monitoring of blood or plasma and of blood coagulation. Droplets of blood or plasma samples are generated in a microfluidic rheometer, and the size of the droplets is highly correlated to the sample viscosity. The microfluidic rheometer system provides viscosity measurements in less than a second and consumes less than 1 µl blood or plasma over an hour period.

BACKGROUND

Abnormalities in blood rheology and coagulation are a major cause of morbidity and mortality worldwide. In the field of trauma care, for example, uncontrollable bleeding caused by coagulopathy (i.e., coagulation abnormalities) is a major cause of preventable death. More than five million people die from trauma every year, accounting for 9% of global annual mortality, and at least one-fourth of trauma patients suffer from coagulopathy. Coagulopathy is also a major complication of sepsis and leads to rapid death. There are over one million cases of sepsis per year resulting in over 250,000 deaths. However, many of these deaths can be prevented through early diagnosis and treatment of coagulopathy. Although efforts have been made to develop tests that are able to monitor blood clotting and the subsequent fibrinolysis process, these tests suffer from low sensitivity and poor reproducibility across laboratories, and have failed to become standardized for acute care. The current routine coagulation assays, such as prothrombin time/international normalized ratio (PT/INR), provide no information on clot evolution and breakdown, thus limiting their ability to diagnose a broader range of coagulation abnormalities. For the most part, these traditional tests examine the accelular (or protein) component of coagulation. The viscoelasticity-based tests, such as throboelastography (TEG) or rotational throboelastometry (ROTEM) have poor reproducibility and accuracy, rendering them somewhat problematic for clinical purposes. They are also expensive and the footprint is large. Furthermore, neither type of test can monitor any changes in the blood before the clots form, such as innate viscosity and its dynamic changes. Neither Thromboelastography (TEG) nor Rotational Thrombelastometry (ROTEM) provide adequate test environments. Lastly, blood viscosity itself is known to change as a result of inflammation, thus making it a suitable candidate for monitoring in a host of cardiovascular and metabolic diseases associated with inflammation. These include but are not limited to sepsis, diabetes, infections, autoimmune diseases, hypertension, and many others.

SUMMARY

The current disclosure is directed to a fully automated microfluidic rheometer system for easy and quick measurement of blood or plasma viscosities in order to continuously monitor blood rheology and viscoelastic properties to include diagnosis of coagulation abnormalities in patients. Whole blood samples from the patient are collected and fed directly into a microfluidic rheometer. The blood or plasma from the sample is mixed with oil in the microfluidic rheometer and emulsifies to form droplets, and the size of the droplets is highly correlated to the sample viscosity. On-chip electrodes sense the differences in dielectric constants once a blood or plasma droplet is passed by. The signal is sent to a computer through a converter, and the size of the droplets is calculated. Once the oil type and feeding pressure are specified, such as by users, the viscosity of blood or plasma can be calculated based on the droplet size and displayed continuously in real-time. The rheometer generates multiple droplets per second depending on the feeding speed of the whole blood samples, thus allowing continuous viscosity measurement within a second. The rheometer is capable of operating on less than 1 µl blood over a one hour period. For a single viscosity measurement, a sample volume as low as 10 nl is enough for reliable viscosity measurements. Droplet lengths remain relatively constant with different sample volumes from 0.1 µl to 100 µl. The microfluidic rheometer can be calibrated and optimized to improve sensitivity and robustness by altering device geometry, channel size, feeding pressures of oil and blood, and oil viscosities.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE PREFERRED EMBODIMENTS

Figure 1:
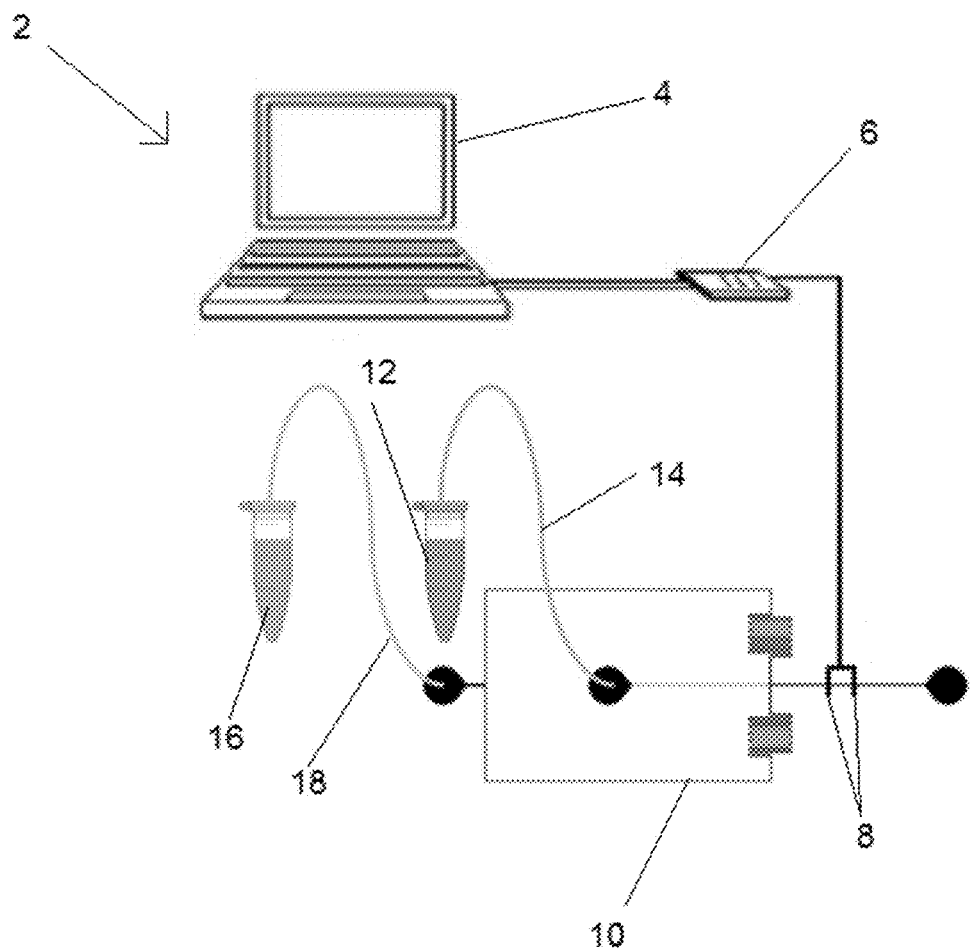
FIG. 1 illustrates schematically a microfluidic rheometer system for real-time viscosity monitoring of blood coagulation including a data collection/readout device, a capacitance-to-digital converter, electrodes for capacitance measurement, a microfluidic rheometer, whole patient blood samples, and oils for droplet generation.

Referring to the figures in detail, FIG. 1 illustrates an exemplary microfluidic rheometer system 2 including a data collection/readout device 4, such as a computer or a portable electronic device, connected to a capacitance-to-digital converter 6, which is connected to electrodes 8. The electrodes 8 measure capacitance generated by droplets in microfluidic rheometer 10, which are formed from whole blood samples provided to the microfluidic rheometer 10 from an aqueous container 12 through aqueous supply line 14 and oil provided to the microfluidic rheometer 10 from an oil container 16 through oil supply line 18. The blood or plasma from the samples and oil meet at the cross junction of the microfluidic rheometer 10 and emulsified to form the droplets. The electrodes 8 sense the differences in capacitance due to changes in dielectric constants once a droplet passes by. The signal is sent to the data collection/readout device 4 through the converter 6, and the size of the droplets is calculated. Once the oil type and feeding pressure are specified by users, the viscosity of blood or plasma can be calculated based on the droplet size and displayed continuously in real-time. The size of the droplets can be determined using an inverted light microscope, a camera, image capture software (not pictured), and image analysis software (not pictured). Alternately, the size of the droplets can be determined using the electrodes 8 and a software program can calculate the speed and size of the droplet.

The microfluidic rheometer 10 may be fabricated from glass wafers using traditional techniques. The glass rheometer 10 may include a first glass wafer that is fabricated to have patterned channels and a second glass wafer that has oil and aqueous inlet holes drilled into it. The two glass wafers may be coated to achieve hydrophobicity (discussed further below) and aligned and bonded. Inlet ports for the aqueous supply line 14 and oil supply line 18 may be created by gluing shoulder washers on top of the desired holes. The aqueous supply line 14 and oil supply line 18 may be PTFE tubes having an inner diameter of 0.022 inches. Pressures at the inlet ports may be measured using a digital pressure gauge.

The microfluidic rheometer system 2 is expected to find wide spread use in hospital and clinics including but not limited to outpatient anticoagulation clinics, general medicine and surgical clinics, cardiac surgery units, various intensive-care units, dialysis units, blood banks, trauma center and emergency rooms. The information provided will help health care providers make rapid decision regarding disease states, disease trajectories, transfusion and blood component utilization decisions, medication and dosage administration decisions, surgical decisions, and more. These health care providers will include Emergency Physicians, Hematologists, Intensivists, Surgeons, Blood Bankers, Diabetologists, Cardiologists, Anesthesiologists, Rheumatologists, Pharmacists, and many other medical and surgical subspecialists for both adult and pediatric patients. The information provided may help reduce the need for blood transfusion, provide personalized and precision medication management for patients at risk for either thrombosis or coagulopathy, and guide general inflammatory and autoimmune disease management.

Figure 2:
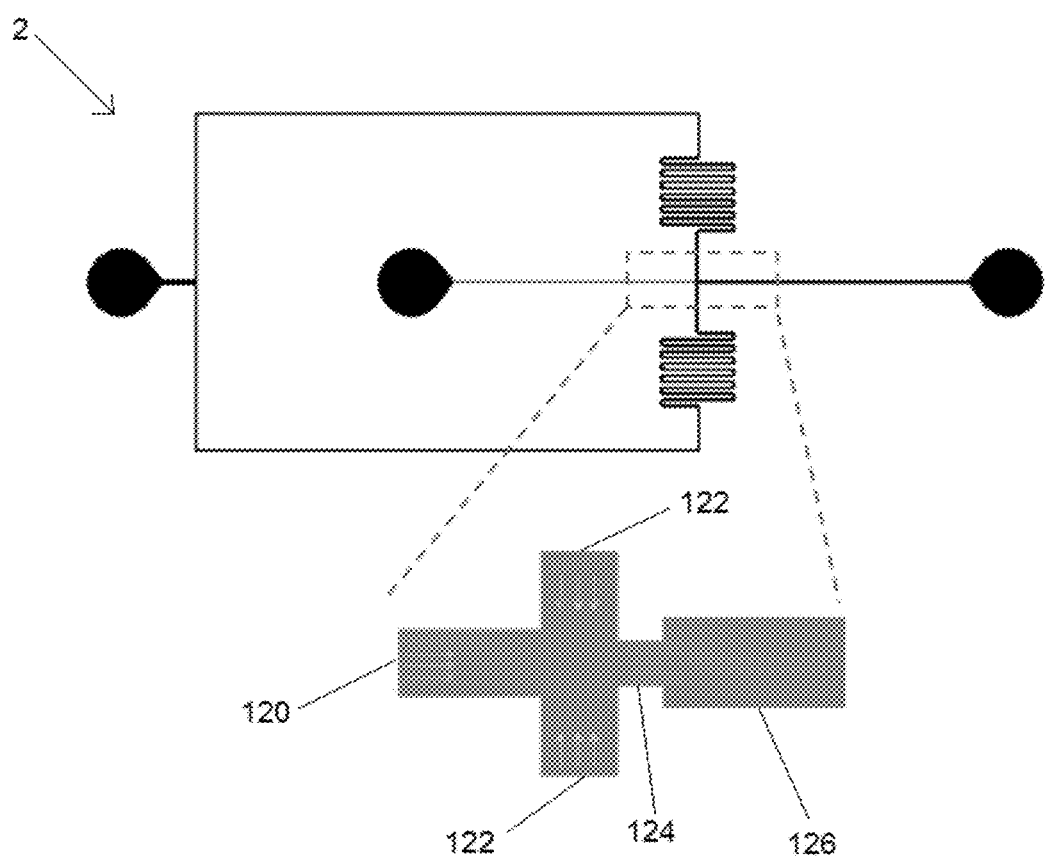
FIG. 2 illustrates the pathways within the microfluidic rheometer in which blood or plasma and fluid are mixed to form droplets.

FIG. 2 illustrates the various pathways within the microfluidic rheometer system 2 by which blood or plasma and fluid are mixed to form droplets. Blood or plasma or an aqueous solution enters through an aqueous inlet 120 that is between 10 and 1000 μm wide. Oil enters through an oil inlet 122 that is generally one to five times as wide as the aqueous inlet 120. The blood or plasma and oil mix into droplets while going through a constriction 124 and then entering a downstream channel 126. The constriction 124 is generally less than or equal in width to the blood inlet, and the downstream channel 126 is wider than the width of the constriction 124 but smaller than two times the size of the aqueous inlet 120. The depth of the downstream channel 126 is preferably on the order of 10 to 100 μm. In an embodiment, the aqueous inlet 120 is 60 μm wide, the oil inlet is 70 μm wide, the constriction is 40 μm long and 40 μm wide, and the downstream channel 126 is 80 μm wide. In some embodiments within the scope of the present disclosure, the aqueous supply line 14 and oil supply line 18 are pressurized, and the feeding pressure of the oil and blood or plasma is determined by the positive pressure settings of the aqueous supply line 14 and the oil supply line 18. In other embodiments within the scope of the present disclosure, a vacuum (not depicted) is attached to an outlet of the downstream channel 126. In such embodiments, the feeding pressures and shear stress of the blood or plasma and oil are created by a negative pressure at the outlet of the downstream channel 126 and can be varied as changing shear can be used as a provocative stimulus for coagulation and to gain further insights into viscosity and coagulation of blood or plasma.

The walls of the constriction 124 and the downstream channel 126 must have sufficient hydrophobicity in order to prevent the droplet size from changing over time. If the walls do not have sufficient hydrophobicity and residuals of the aqueous solutions adhere to the walls, the aqueous residuals may change the hydrophobicity of the walls and result in inconsistency in droplet size over time. For example, in some embodiments, polydimethylsiloxane (PDMS) may coat the walls of the constriction 124 and the downstream channel 126 to provide sufficient hydrophobicity. In other examples, 2 μm of parylene-C may coat the walls of the constriction 124 and the downstream channel 126 to provided sufficient hydrophobicity.

Figure 3:
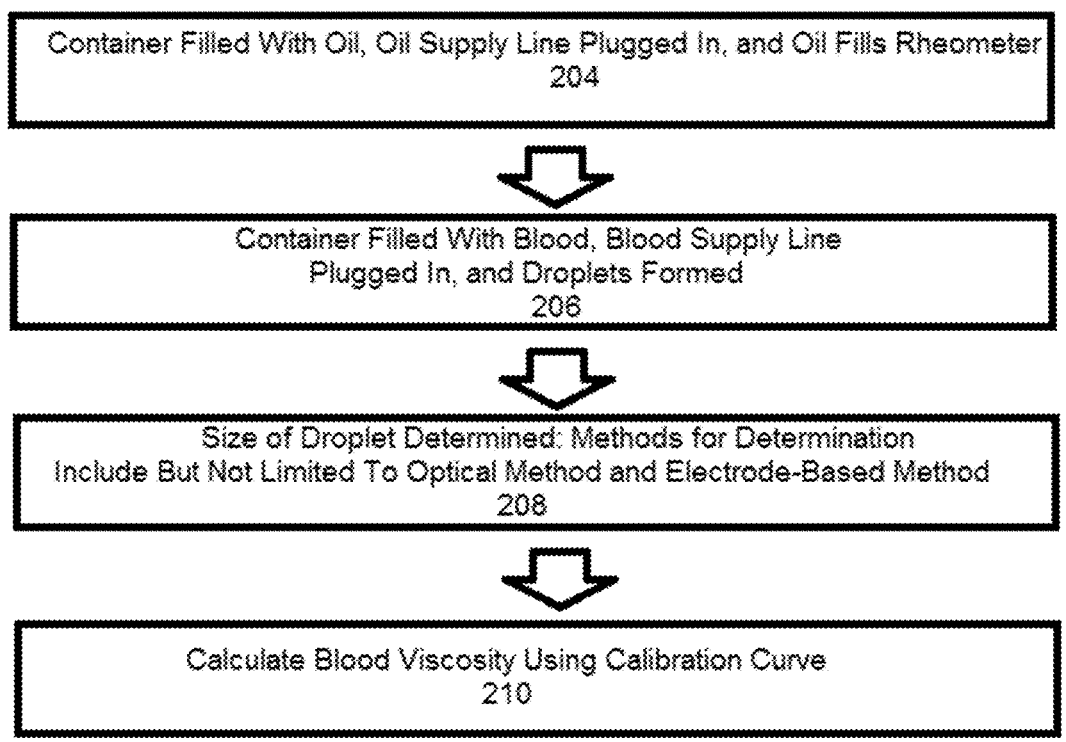
FIG. 3 is a flow chart illustrating a method of providing real-time viscosity data via use of a microfluidic rheometer system of the present disclosure.

FIG. 3 is a flow-chart illustrating a method of providing real-time viscosity data 202 via use of the microfluidic rheometer system 2. At box 204, the oil container 16 is filled with surfactant-added oil, and the oil supply line 18, which may be pressurized, is plugged into the microfluidic rheometer 10. Mineral oils may be used as the surfactant-added oil, and/or the selection of oil may be dictated by factors such as optimized wetting or interfacial tension effects. Sufficient time is allowed to pass for the oil supply line 18 and the oil inlet 122, constriction 124, and downstream channel 126 to fill with the oil. This generally takes less than one minute depending on channel dimensions. At box 206, the aqueous container 12 is filled with either fresh whole blood or recalcified citrated whole blood, and the aqueous supply line 14, which may be pressurized, is plugged into the microfluidic rheometer 10. Through additional filtration or microfluidic channels (not shown), plasma can be separate from whole blood if desired. As the blood or plasma from the blood mixes with the oil, droplets begin to be formed. Multiple droplets are generated per second by the microfluidic rheometer 10, thus allowing continuous viscosity measurement within a second. At box 208, the size of a droplet is determined. This may be done using an optical method or an electrode-based method. If the optical method is used, an inverted light microscope, a CCD camera, and image capture software such as OCapture is used to record the droplet generation at the downstream channel 126, and the size of the droplet is measured using an image analysis software such as ImageJ. In some embodiments, the inverted light microscope may have a 10× objective lens. If the electrode-based method is used, the electrodes 8 receive a peak signal (i.e., sense the differences in capacitance due to changes in dielectric constants) when a droplet passes through, the signal is sent to the data collection/readout device 4 through the capacitance-to-digital converter 6, and a LABVIEW (Trademark) or other development environment program is used to receive the signal and calculate the speed and size of the droplet. At box 210, a calibration curve is used to calculate blood or plasma viscosity based on droplet sizes. The calibration curve can be determined using glycerol/water solutions within the microfluidic rheometer 10. In some embodiments, the calibration curve shows a linear fitting law between log of droplet length versus log of viscosity. For instance, according to Hagen-Poiseuille law, $\Delta P \: \alpha \: \eta Q$ (where $\Delta P$ is pressure difference, $\eta$ is solution viscosity, and Q is flow rate), is considered valid for an aqueous inlet channel of a fixed channel geometry. A user may provide oil type and feeding pressures for use in calculating the blood or plasma viscosity, and the range and sensitivity of the microfluidic rheometer can be optimized for different applications by changing device geometry, oil viscosity, and feeding speeds of the oil and blood or plasma. A working range of feeding pressures is governed by the ratio of aqueous feeding pressure to oil feeding pressure (AIP/OIP). Sensitivity of the microfluidic rheometer of the present disclosure increases with increasing AIP/OIP. In some embodiments, droplet generation occurs at AIP/OIPs from 0.25 to 0.80 and droplet distortion occurs at AIP/OIPs above 0.72.

Optionally, the calibration curve is input into a LABVIEW or similar development environment program so that the viscosity of the blood or plasma is automatically calculated and displayed. The information may further be transmitted to the Internet or cloud storage to enable a doctor to check in on a patient and to support big data analytic studies on blood clotting disorders. The total blood or plasma consumption of the rheometer for one-hour continuous measurement is typically less than 1 µl.

The platform may include multiple channels for multiplex testing of blood or plasma, allowing specific coagulation or inflammatory disorders to be more precisely defined. Using this strategy, channels may be pre-coated with various pro or anticoagulants or various pro and antiinflammatory agents which interact with either the cellular (red cell, white cell, platelet) component of blood or the acellular (protein) component. Alternatively, mixing chambers can be created which allow blood or plasma to be mixed with these agents prior to or after oil emulsification.

Figure 4:
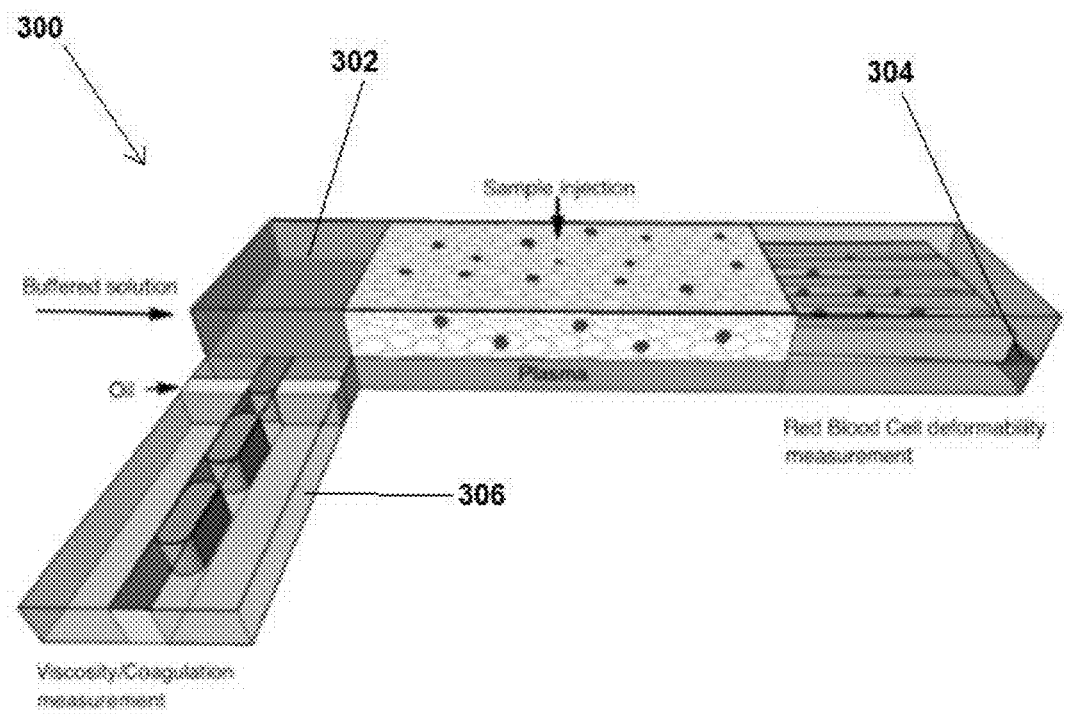
FIG. 4 illustrates a microfluidic rheometer system having a red blood cell deformability measurement system.

FIG. 4 depicts integration of a red blood cell deformability measurement system 302 into a microfluidic rheometer system 300. Red blood cell deformability is key in inflammation response processes and has been found to be associated with outcomes in cardiovascular disease, hypertension, sepsis, and other health related issues. Additionally, reduced deformability of red blood cells is a severe storage lesion in blood used for transfusion and has been associated with adverse outcomes. In the embodiment depicted in FIG. 4, the microfluidic rheometer system 2 depicted in FIG. 1 is adapted to measure plasma viscosity and is identified as a viscosity measurement system 306. A red blood cell deformability measurement system 302 is on top of the viscosity measurement system 306. The plasma sample passes through a separation membrane 304 before reaching the viscosity measurement system 306. In the red blood cell deformability system 302, the red blood cells flow through an obstructed path, and the stopping point of the red blood cells correlates to their deformability. In other embodiments, the viscosity measurement system 306 is adapted for whole blood samples, and half of the whole blood sample is delivered to the viscosity measurement system while the other half goes into the red blood cell deformability section.

Figure 5:
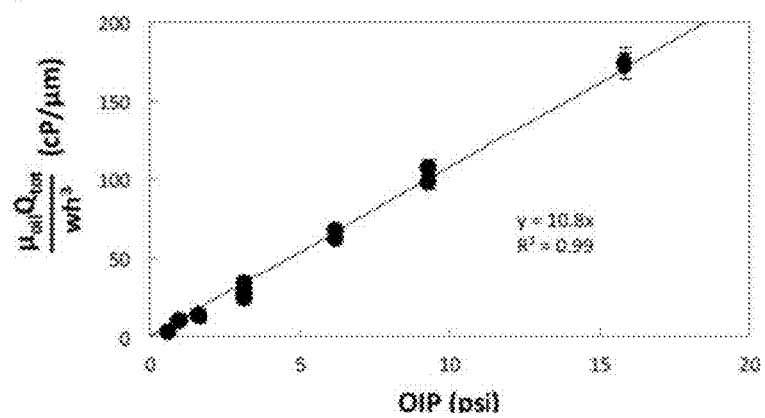
FIG. 5 is a graph illustrating the relationship between oil-inlet pressure (OIP), device geometry, and flow rate.

FIG. 5 is a graph illustrating the relationship between oil-inlet pressure (OIP), device geometry, and flow rate. Empirically, the relationship between OIP, device geometry, and flow rate, assuming w is the width of the channels, h is the channel depth, and $Q_{tot}$ is the total flow rate, was determined to be $OIP=(\mu_{oil}Q_{tot})/(10.8 \: wh^3)$. The data supporting this empirical determination is discussed in Example 3 below.

EXAMPLES

Example 1

The relationship between the length of droplets and the ratio of aqueous-inlet to oil-inlet pressure (AIP/OIP) in the microfluidic rheometer system of the present disclosure was studied empirically. Glycerol and deionized water solutions with varying glycerol mass fraction were prepared for viscometer calibration. Light mineral oil with 5 wt % ABIL® EM 90 and heavy mineral oil with 5 wt % ABIL® EM 90 were prepared and used as the continuous phase for droplet generation. The cell culture medium contained M9 minimal medium with 36 g/l glucose (2 mM MgSO4, 0.1 mM CaCl2), 33.7 mM Na2HPO4, 22 mM KH2PO4, 8.55 mM NaCl, 9.35 mM NH4Cl, 3.6% glucose). Blood serum and blood plasma were Prepared from whole blood using standard protocols. Boger fluid (i.e., constant viscosity elastic fluid) was prepared by dissolving 8000 ppm polyethylene glycol in 78% glycerol solution. The viscosities of all aqueous solutions and oil/surfactant mixtures at 25° C. were measured on a cone-and-plate rheometer. The droplet-based microfluidic viscometer was used to measure the glycerol/water solutions. After connecting the oil reservoir to the chip, pressure was applied to the oil inlet to fill the channels with oil. Then, the aqueous sample was fed into the device and droplets were generated. Recordings and measurement were made after droplet generation become steady (typically in less than 1 minute). The image stacks were analyzed using ImageJ to measure the length and speed of the droplets, the spacing between two droplets and the generation time for one droplet.

The results showed that the length of the droplets ($L_d$) is highly correlated to the aqueous-phase viscosity ($\mu_{aq}$) at high ratios of aqueous-inlet to oil-inlet pressure (AIP/OIP), yielding a linear relationship between $\mu_{aq}$ and $1/(L_d-L_c)$ where $L_c$ is the minimal obtainable droplet length. Theoretical analysis verifies this linear relationship, and the resulting equations can be used to optimize the device geometry (i.e., channel widths, depths and lengths). The applicable range of viscosity measurements depends on the oil-phase viscosity ($\mu_{oil}$), and viscosities within the range of 0.01 µoil to 10 µoil can be measured reliably with less than 5% error.

Example 2

The lengths of droplets were measured when different volumes of aqueous solution (µaq=72.5 cP) were pipetted into the device. All measurements were conducted at OIP=3.17 psi and AIP/OIP=0.65.

Figure 6:
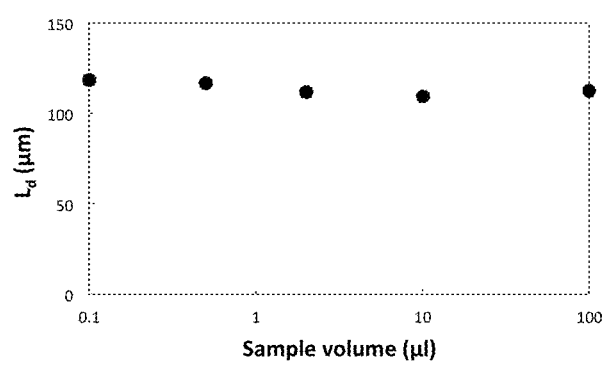
FIG. 6 is a graph illustrating the relationship between the lengths of droplets and different volumes of aqueous solution.

As shown in FIG. 6, the droplet lengths remain relatively constant with different sample volumes from 0.1 µl to 100 µl.

Example 3

The relationship between oil-inlet pressure (OIP), device geometry, and flow rate was studied empirically to assist with design considerations of the microfluidic rheometer system of the present disclosure. Data was collected, shown below, on a total of eight rheometer systems with different geometries using two different oil viscosities and four different OIPs.

| Device # | h (μm) | w1 (μm) | w2 (μm) | w3 (μm) | L3 (μm) | oil viscosity (cP) |
|---|---|---|---|---|---|---|
| 1 | 5 | 15 | 25 | 25 | 8000 | 37 |
| 2 | 22.5 | 47.5 | 55 | 55 | 8000 | 37 |
| 3 | 22.5 | 47.5 | 55 | 55 | 8000 | 147 |
| 4 | 22.5 | 47.5 | 55 | 55 | 4000 | 37 |
| 5 | 41 | 74 | 82.5 | 82.5 | 8000 | 37 |
| 6 | 44 | 80 | 88 | 88 | 8000 | 147 |
| 7 | 60 | 94 | 111 | 111 | 8000 | 37 |
| 8 | 175 | 230 | 230 | 230 | 8000 | 37 |

Based on this data, a relationship between OIP, device geometry, and flow rate was determined. Assuming w is the width of the channels, which are comparable in width, h is the channel depth, and $Q_{tot}$ is the total flow rate, the relationship is:

$$OIP = (\mu_{oil} Q_{tot})/(10.8\ wh^3)$$

This equation is applied in the table below.

| Device # | OIP (psi) | $\mu_{oil}Q_{tot}/(wh^3)$ (cP/μm) |
|---|---|---|
| 1 | 3.2 | 28.9 |
| 1 | 15.8 | 172.5 |
| 2 | 1.7 | 13.1 |
| 2 | 3.2 | 28.7 |
| 2 | 6.1 | 62.2 |
| 2 | 9.3 | 97.7 |
| 3 | 3.2 | 33.6 |
| 3 | 6.1 | 67.4 |
| 3 | 9.3 | 107.5 |
| 4 | 1.6 | 14.0 |
| 5 | 3.2 | 24.4 |
| 6 | 3.2 | 25.3 |
| 6 | 3.2 | 26.1 |
| 7 | 3.2 | 24.1 |
| 8 | 1.0 | 9.9 |

The empirical data closely matches the equation, as shown in FIG. 5.

Accordingly, $OIP = (\mu_{oil} Q_{tot})/(10.8\ wh^3)$ can be considered a valid equation for a wide range of device geometry, oil viscosity, and operating pressures.

What is claimed is:

1. A microfluidic rheometer system comprising:
   a data collection and readout device configured to measure a property of droplets in the microfluidic rheometer;
   a first oil inlet by which oil enters the microfluidic rheometer and a second oil inlet by which oil enters the microfluidic rheometer, the first oil inlet positioned across from the second oil inlet, wherein the first oil inlet and the second oil inlet are each connected to an oil supply line that is connected to an oil container; and
   an aqueous inlet by which blood or aqueous solution enters the micrometer, wherein the aqueous inlet is connected to an aqueous supply line that is connected to an aqueous container.

2. The microfluidic rheometer system of claim 1, wherein the microfluidic rheometer further comprises:
   a constriction downstream of the first oil inlet, the second oil inlet, and the aqueous inlet;
   a downstream channel downstream of the constriction.

3. The microfluidic rheometer system of claim 2, wherein:
   a width of the first oil inlet is one to five times the size of a width of the aqueous inlet;
   a width of the constriction is less than or equal to the width of the aqueous inlet; and
   a width of the downstream channel is greater than the width of the constriction but less wide than two times the width of the aqueous inlet.

4. The microfluidic rheometer system of claim 1, wherein at least one of the oil supply line and the aqueous supply line is pressurized.

5. The microfluidic rheometer system of claim 1, further comprising:
   an inverted light microscope and camera operatively connected to the microfluidic rheometer to procure images of droplets within the microfluidic rheometer;
   an image capture software operatively connected to the inverted light microscope and the camera in order to capture the images of droplets within the microfluidic rheometer.

6. The microfluidic rheometer system of claim 1, further comprising:
   a software program to calculate a speed and size of a droplet operatively connected to the electrodes.

7. The microfluidic rheometer system of claim 2, wherein the oil and the blood or aqueous solution meet upstream of the constriction.

8. The microfluidic rheometer system of claim 1, further comprising multiple channels for multiplex testing of blood or plasma.

9. The microfluidic rheometer system of claim 8, wherein the multiple channels are pre-coated with at least one of a procoagulant agent, an anticoagulant agent, a proinflammatory agent, and an anti-inflammatory agent.

10. The microfluidic rheometer system of claim 1, further comprising mixing chambers allowing blood or plasma to mix with at least one of a procoagulant agent, an anticoagulant agent, a proinflammatory agent, and an anti-inflammatory agent.

11. The microfluidic rheometer system of claim 1, wherein the microfluidic rheometer is fabricated from a first glass wafer having patterned channels bonded to a second glass wafer having an oil inlet and an aqueous inlet.

12. The microfluidic rheometer system of claim 1, wherein the walls of the constriction and the downstream channel 126 are coated with a hydrophobic material.

* * * * *